United States Patent [19]

Kyriacou et al.

[11] Patent Number: 4,533,454

[45] Date of Patent: Aug. 6, 1985

[54] ELECTROLYTIC CELL COMPRISING STAINLESS STEEL ANODE, BASIC AQUEOUS ELECTROLYTE AND A CATHODE AT WHICH TETRACHLORO-2-PICOLINATE IONS CAN BE SELECTIVELY REDUCED IN HIGH YIELD TO 3,6-DICHLOROPICOLINATE IONS

[75] Inventors: Demetrios Kyriacou, Salonica, Greece; Donald N. Brattesani, Oakland, Calif.

[73] Assignee: The Dow Chemical Company, Midland, Mich.

[21] Appl. No.: 305,822

[22] Filed: Sep. 28, 1981

[51] Int. Cl.$^3$ ............................ C25B 11/00; C25B 3/00
[52] U.S. Cl. ......................................... 204/272; 204/72; 204/73 R; 204/284

[58] Field of Search ............... 204/59 R, 72, 292, 272, 204/284, 73 R

[56] References Cited

U.S. PATENT DOCUMENTS

| | | | |
|---|---|---|---|
| 4,140,593 | 2/1979 | Mitzlaff | 204/59 R |
| 4,217,185 | 8/1980 | Kyriacou et al. | 204/73 R |
| 4,242,192 | 12/1980 | Dunning et al. | 204/213 |

*Primary Examiner*—John F. Niebling
*Attorney, Agent, or Firm*—Robert R. Stringham

[57] ABSTRACT

An important increase in the yield of 3,6-dichloropicolinic acid prepared by electrolytic reduction of tetrachloro-2-picolinic acid (in basic, aqueous solution, at a silver cathode) results when a stainless steel anode is used, rather than those (graphite, e.g.) taught in the prior art (U.S. Pat. No. 4,217,185).

4 Claims, No Drawings

ELECTROLYTIC CELL COMPRISING STAINLESS STEEL ANODE, BASIC AQUEOUS ELECTROLYTE AND A CATHODE AT WHICH TETRACHLORO-2-PICOLINATE IONS CAN BE SELECTIVELY REDUCED IN HIGH YIELD TO 3,6-DICHLOROPICOLINATE IONS

BACKGROUND OF THE INVENTION

Production of 3,6-dichloropicolinic acid (3,6-D), a highly active plant growth regulator, by electrolytic reduction of tetrachloro-2-picolinic acid ("tet-acid") at a silver cathode in basic, aqueous solution is disclosed in U.S. Pat. No. 4,217,185 (the disclosure of which is hereby incorporated herein for all purposes sanctioned by United States patent laws).

The cathode has a surface layer of silver microcrystals formed by the electrolytic reduction of colloidal, hydrous, silver oxide particles in the presence of an aqueous base. The presence of other noble metals is not beneficial and the presence of base metals (nickel and copper, most notably) definitely lowers the activity of the cathode. However, other conductive metals, including stainless steel, may serve as a substrate on which the silver layer is formed, provided that the substrate metal not be subjected to anodization (as in a preferred method of forming the precursor silver oxide particles).

Inert electrode materials are generally suitable for the anode to be used in conjunction with the silver cathode, but in order to attain 3,6-D yields of 90% or more, it is necessary, according to the patent, to employ anodes consisting essentially of graphite. Other anode materials are believed to encourage decarboxylation ("Kolbe type" oxidation of polychloropyridine carboxylate anions).

In the course of developing the patented process on a pilot plant scale, it has been found that 3,6-D yield and purity are sensitive to the type of graphite the anode is made of. Furthermore, even the most suitable graphite found (Union Carbide grade ATL graphite) undergoes spalling and a drop-off in 3,6-D yield and purity is experienced as the anode ages in use. This is readily corrected by replacing the anode with a fresh one, but that results in higher capital and operating expenses. Accordingly, it is apparent that an otherwise suitable anode material less susceptible to deleterious alterations in prolonged use would be highly desirable.

OBJECTS OF THE INVENTION

The primary object of the invention is to provide a superior anode for use with a cathode at which tetrachloro-2-picolinic acid in aqueous, basic solution can be selectively reduced to 3,6-dichloropicolinic acid in high yield.

An ancillary object is to provide an electrolytic cell adapted for the conversion of the tet-acid to 3,6-D and incorporating the improved anode.

A particular object is to provide such a cell in which the cathode is the specific silver cathode disclosed in the foregoing '185 patent (and claimed, as such, in U.S. Pat. No. 4,242,183).

A further object is to avoid the costs and processing interruptions associated with periodic replacement of graphite anodes (and the consequent fluctuations in the purity of the 3,6-D product).

An additional object is to eliminate the source of the trace metal impurities known to be present in available graphites—which impurities are believed responsible for the apparent need for periodic acid washing (of the cathode) disclosed in the '185 patent.

Still other objects will be made apparent to those skilled in the art by the following specifications and claims.

SUMMARY OF THE INVENTION

It has now been discovered that the foregoing objects can be realized by utilizing stainless steel as the anode material. (In view of the teachings and provisos of the '185 patent and the fact that stainless steels comprise nickel, iron and chromium, the suitability of such steels for the present purpose is considered surprising.)

More specifically, the present invention is an electrolytic cell and the use thereof to reduce polychloropicolinic acids. That is, said cell and use may be defined as follows:

The cell of the invention may be broadly defined as an electrolytic cell comprising a stainless steel anode and a cathode at which tetrachloro-2-picolinate anions in basic, aqueous solution can be selectively reduced in high yield to 3,6-dichloro-2-picolinate anions.

The cell of the invention may be less broadly defined as also comprising a basic, aqueous electrolyte. As contemplated by this definition, the electrolyte is a working component of the cell, not the material worked on (reduced or oxidized) by the cell. In those instances in which electrolysis of water (formation of hydrogen at the cathode and/or of oxygen at the anode) occurs as a side or co-reaction, the unconverted portion of the aqueous base still functions as the electrolyte.

The process of the invention is the use of the foregoing cell in the electrolytic process for the co-production of oxygen and polychloropicolinate anions of the structure

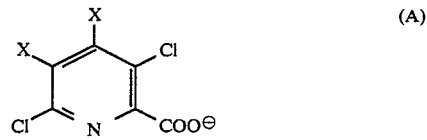

(A)

wherein one X is H and the other is H or Cl, which comprises
providing a solution in an aqueous base of a polychloropicolinic acid of the structure

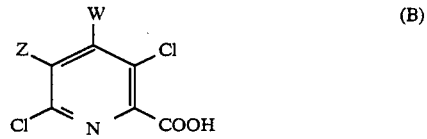

(B)

wherein both Z and W are Cl, or one is Cl and the other is H, and, while agitating said solution, passing an electric current therethrough from said anode to said cathode, said solution having a temperature within the range of from about 5° to about 60° C., a pH of about 13 or more and containing at least 0.08 hydroxyl ions per chloride ion present therein, said cathode having a potential, relative to a saturated calomel reference electrode, of from about −0.8 to about −1.8 volts and said anode having a potential, relative to the cathode, such that the density of said current is from about 0.005 to about 0.085 amperes per $cm^2$ of projected cathode surface,
thereby forming anions of said polychloropicolinic acid (A) at said cathode and oxygen at said anode.

The foregoing limitations as to temperature, pH, $OH^-$ to $Cl^-$ ratio and electrode potential are recited as essential to operability and not as distinguishing the present process invention from that disclosed in the '185 patent. Correspondingly, the process of the present invention may be generally regarded as the improvement in the patented process which comprises employing stainless steel as the anode material.

The cathode employed in the present invention may be defined as above or as a cathode means for the electrolytic reduction of the tet-acid (in basic solution) to 3,6-D in yields of 90 mole percent or more. Either definition of the cathode reads on (but is not to be construed as limited to) the (highly preferred) silver cathode employed in the process of the '185 patent.

DETAILED DESCRIPTION

Suitable anode materials for the practice of the present invention are those alloys of chromium, nickel and iron—commonly designated as stainless steels—which are highly resistant to corrosion by basic, aqueous chloride brines at temperatures up to about 60° C. (The resistance to corrosion by basic brines at various $OH^-$ and $Cl^-$ concentrations is well known for a wide range of stainless steel compositions.) The presently most preferred such material is 316 stainless steel (which has the composition 0.11 wt. % C, 17–19 wt. % Cr, 7–11 wt. % Ni and 2–4 wt. % Mo (the balance consisting essentially of Fe). Other specific stainless steels believed suitable are grades 302 through 310 and 320, 321 and 403.

The preferred cathode for the practice of the present invention is one having a surface layer of silver microcrystals formed by the electrolytic reduction of colloidal, hydrous silver oxide particles in the presence of an aqueous base. The method of preparing this type of cathode is disclosed (and claimed) in U.S. Pat. No. 4,242,183. However, any other cathode capable of selectively reducing tetrachloro-2-picolinate anions to 3,6-dichloro-2-picolinate anions in yields of at least 90 mole percent may be employed with the stainless steel anode.

Polychloropicolinic acids of the preceding formula (B) may be reduced to the corresponding acids of formula (A) in the manner described in U.S. Pat. No. 4,217,185 but employing the cell of the present invention, i.e., a cell comprising a stainless steel anode, a basic aqueous electrolyte and a cathode having the capability specified in the immediately preceding paragraph.

The electrodes in the latter cell may be of any configuration, the same or different. However, it is preferred that the cathode and anode take the form of concentrically disposed cylinders.

Similarly, each electrode may be formed of a solid bar or sheet, a screen or "expanded" sheet. High surface area forms, such as screens or other foraminous sheets, for example, are preferred, particularly in those applications in which the cell contents are agitated.

It should be noted that the anode does not have to be a monolithic body of metal. It is only necessary that those portions of the anode surface layer subject to contact with the cell contents consist of stainless steel (and that the anode as a whole is otherwise suitable).

The utility of the present cell of course is not limited to reductions of polychloropicolinic acids. It may be employed for the reduction (or oxidations) of any substrate material which is soluble in an aqueous base and does not (as such or in its reduced or oxidized form) detrimentally react with the electrolyte to an intolerable extent. Where appropriate, the cell may also comprise a diaphragm (or an equivalent anolyte/-catholyte separating means) and/or agitation of the cell contents may be dispensed with. Such other modifications, or ancillary apparatus as may be necessary or appropriate to utilization of the present cell in any particular electrochemical application will be apparent to those skilled in the art of electrochemistry. Similarly, the appropriate values for such process parameters as temperature, electrode potentials, pH, choice of base, base concentration, etc., will also be apparent to those skilled in the art. For those less knowledgeable, the following textbook should be helpful. Basics of Electroorganic Synthesis; D. K. Kyriacou. Wiley-Interscience Publications (1981). John Wiley & Sons, New York, N.Y.

Any otherwise suitable source of hydroxyl and counter ions may be employed as the base in the cell (and process) of the present invention. However, alkali metal hydroxides are preferred, most notably KOH or NaOH, the latter being particularly preferred.

The term "otherwise suitable" of course implies that the base employed does not detrimentally react with any component of the cell itself or any other component of the cell contents to an intolerable degree.

A restraint is imposed on base concentration by the susceptibility of at least some stainless steels to corrosion at low hydroxide concentrations. In the case of 316 stainless, the hydroxide concentration should not be allowed to drop below about 1.0 wt. %, particularly at temperatures above normal ambient temperatures.

It should be noted that the term "aqueous base" is not intended to exclude the presence in the anolyte and/or catholyte of other substances, such as, for example, organic co-solvents or soluble salts, which do not detrimentally affect obtention of the desired product.

The following examples are for purposes of illustration and are not to be construed as limiting the scope of the present invention in a manner inconsistent with the claims appended to this specification.

EXAMPLES

Example 1

To a 200 ml electrolytic beaker equipped with a Teflon-coated magnetic stirring bar, a cylindrical silver screen cathode, a cylindrical, imperforate 316SS anode, a Luggin capillary tube fitted with a standard calomel electrode (SCE) and a thermometer, was added enough 1/1, v/v, conc. $HCl/H_2O$ to fill the cell (Luggin capillary removed). The aqueous HCl was stirred in the cell for 10 min. followed by draining, rinsing well with reverse osmosis purified (RO) water, then filling with 108.24 gms. of 7.0 wt. % NaOH (mercury grade caustic; solution prepared with RO water). The cathode was anodized to $+0.6V$ vs SCE for 5 min. (3 amps maximum), followed by cathodization to $-1.3V$ vs SCE (3 amps maximum), giving a background current of 0.5 amperes. The tet acid (11.76 g, 0.0451 moles) was added portionwise over 3.5 hours by masticating each 2 gm portion with cell liquor, then returning the resulting slurry to the bulk of the solution. The electrolysis proceeded as follows (the cathode potential relative to the SCE remaining at −1.3 volts throughout, except during periodic anodization intervals as noted) for a total reaction time of 5.4 hours (382−57=325 minutes)):

TABLE I

| Elapsed Time (Minutes) | Temp. (°C.) | Cell Current Amps | Comments |
|---|---|---|---|
| 0 | 20.5 | — | 1/1, v/v, conc. HCl/H₂O added for cleansing. |
| 10 | 20.0 | — | Drained aq. HCl, rinsed well w/R.O. H₂O; 7.0% NaOH added. |
| 16 | 20.0 | — | Anodization: +0.6 v/5 min./0.35 amps final. |
| 56 | 22.0 | 1.1 | Anodization complete. |
| 57 | 22.0 | 0.5 | Adding 2 gms TA.[1] |
| 62 | 23.5 | 4.3 | Addition complete. |
| 87 | 23.5 | 1.1 | Adding 2 gms TA. |
| 91 | 25.0 | 4.2 | Addition complete. |
| 117 | 25.0 | 1.3 | Adding 2 gms TA. |
| 120 | 26.0 | 4.2 | Addition complete. |
| 147 | 26.0 | 1.2 | Anodization: +0.6 v/9 min./0.48 amps final. |
| 174 | 26.0 | 2.1 | Anodization complete. |
| 177 | 26.0 | 1.0 | Adding 2 gms TA. |
| 180 | 27.5 | 4.6 | Addition complete. $E_{cell}$ = 2.4 v. |
| 207 | 27.0 | 0.8 | Adding 2 gms TA. |
| 210 | 28.5 | 4.7 | Addition complete. |
| 237 | 28.0 | 0.9 | Anodization: +0.6 v/8 min./0.48 amps final. |
| 263 | 28.0 | 1.6 | Anodization complete. |
| 267 | 28.0 | 0.8 | Adding 0.6 gm TA. |
| 269 | 28.0 | 2.3 | All TA added. |
| 327 | 26.5 | 0.4 | Anodization: +0.6 v/9 min./0.7 amps final. |
| 352 | 27.0 | 1.4 | Anodization complete. |
| 382 | 25.5 | 0.48 | STOP; suspended solid in cell liquor. |

Note:
[1] tet-acid.

The cell liquor was filtered by suction through celite, then stored in the cold (5° C.) for 65 hours. The cell liquor (pH 12.56) was acidified with conc. HCl to pH 1.00, and the resulting mixture was extracted with $CH_2Cl_2$ (3×100 ml; 9×50 ml). The combined organic layer was dried over anhydrous $Na_2SO_4$ (5 min.), filtered, and the solvent was removed at reduced pressure (rotary evaporator, 50° C., 30 min.) to give 8.65 gms of white crystalline solid.

The latter solid was found (by Gas/Liquid Phase Chromatography) to be 98.458 wt. % 3,6-dichloro-2-picolinic acid. The theoretical yield of 100% 3,6-D was calculated as $(0.98458 \times 8.65) \div (191.96 \times 0.04508) = 98.4\%$.

Example 2

(Comparison of SS and graphite anodes)

In essentially the manner of Example 1, a series of runs was carried out using three different grade graphite anodes and one grade (316) stainless steel anode. The results are given in Table II below:

TABLE II

The Effect of Different Anode Materials

| Run | Anode[2] | 3,6-D Yield (%) | PRODUCT DISTRIBUTION (WT. %)[1] | | | | Tet-Acid Accountability[3] |
| | | | 3,6-D | MCPA | 4,5-DCPA | TCPA | |
|---|---|---|---|---|---|---|---|
| 1 | ATL | 93.8 | 98.0 | 0.8 | 0.6 | — | 99.4 |
| 2 | ATL | 97.0 | 99.0 | 1.1 | 0.4 | — | 100.5 |
| 3 | ATL | 97.0 | 99.0 | 1.1 | 0.5 | — | 100.6 |
| 4 | ATL | 95.0 | 98.3 | 1.2 | 0.7 | — | 100.2 |
| 5 | ATL | 96.5 | 99.2 | 1.0 | 0.5 | — | 100.8 |
| 6 | ATL | 96.0 | 98.6 | 1.0 | 0.7 | — | 100.3 |
| 7 | ATL | 95.7 | 98.3 | 1.0 | 0.5 | — | 99.8 |
| 8 | AGSR | 67.6 | 74.0 | 2.7 | 1.9 | 17.2 | 95.8 |
| 9 | ECV | 57.0 | 73.7 | 4.5 | 2.6 | 13.2 | 94.3 |
| 10 | 316SS | 96.5 | 98.0 | 2.3 | 0.7 | — | 101.0 |
| 11 | 316SS | 97.5 | 98.6 | 2.2 | 0.6 | — | 101.4 |
| 12 | 316SS | 98.4 | 98.5 | 1.6 | 0.5 | — | 100.6 |
| 13 | 316SS | 100.0 | 98.1 | 1.6 | 0.8 | — | 100.5 |
| 14 | 316SS | 99.7 | 98.4 | 1.4 | 0.9 | — | 100.7 |
| 15 | 316SS | 100.0 | 99.0 | 1.0 | 1.0 | — | 101.0 |
| 16 | 316SS | 99.4 | 98.0 | 0.9 | 0.8 | — | 99.7 |
| 17 | 316SS | 99.4 | 98.0 | 1.0 | 0.8 | — | 99.8 |
| 18 | 316SS | 99.8 | 98.6 | 1.6 | 0.5 | — | 100.7 |
| 19 | 316SS | 99.6 | 98.0 | 1.3 | 0.5 | — | 99.7 |
| 20 | 316SS | 99.3 | 98.0 | 1.3 | 1.0 | — | 100.3 |
| 21 | 316SS | 97.7 | 98.0 | 1.3 | 0.8 | — | 100.1 |

Notes:
[1] 3,6-D = 3,6-dichloropicolinic acid; 4,5-DCPA = 4,5-dichloropicolinic acid; MCPA = monochloropicolinic acid; TCPA = trichloropicolinic acids.
[2] ATL = medium priced general purpose graphite with consistent medium grain size.
AGSR = economical, general purpose graphite of variable grain size.
ECV = graphite for high purity applications possessing small grain size; ash level of ca. 50 ppm.
316SS = stainless steel grade 316.
ATL, AGSR, and ECV are graphite materials produced by the Union Carbide Corporation, Chicago, Ill.
[3] % of starting material accounted for by products.

It will be seen that the yield of 3,6-D (of essentially the same purity) was consistently higher with the stainless steel anode. The average yield for the seven runs with (fresh) ATL graphite anodes was 95.86% and the average for the twelve runs with the (same) stainless steel anode was 98.94%. Ignoring the very minor difference in average accountability for the two series, at least a 3% higher yield is indicated for the stainless steel anode. For a process operated on a commercial scale, this of course is an important improvement When the same ATL graphite anode was used for thirteen successive runs, a drop in product yield and purity to 83% of 91% pure 3,6-D resulted. (A run made with the same cell but with a fresh ATL anode resulted in a 99%-yield of 99% pure 3,6-D.) In contrast, a 97.7% yield of 98% pure 3,6-D was obtained from run number 12 (Table II) with the stainless steel anode.

What is claimed is:

1. An electrolytic cell comprising
(a) a stainless steel anode, and
(b) a silver cathode having a surface layer of silver microcrystals formed by electrolytic reduction of colloidal, hydrous silver oxide particles in the presence of an aqueous base and being capable of effecting the selective reduction of tetrachloro-2-picolinate anions to 3,6-dichloro-2-picolinate anions in a yield of at least 90% when said cathode is employed in conjunction with a graphite anode in an electrolytic cell containing a basic, aqueous electrolyte in which said tetrachloropicolinate is dissolved.

2. The cell of claim 1 in which said anode and cathode are of a cylindrical configuration and one is disposed concentrically within the other.

3. The cell of claim 2 in which at least one of said anode and cathode is in the form of a foraminous sheet.

4. The cell of claim 3 in which said sheet is a screen.

* * * * *